(12) United States Patent
Villarreal

(10) Patent No.: US 6,870,109 B1
(45) Date of Patent: Mar. 22, 2005

(54) SYSTEM AND DEVICE FOR REDUCING SIGNAL INTERFERENCE IN PATIENT MONITORING SYSTEMS

(75) Inventor: Richard A. Villarreal, West Richland, WA (US)

(73) Assignee: Cadwell Industries, Inc., Kennewick, WA (US)

( * ) Notice: Subject to any disclaimer, the term of this patent is extended or adjusted under 35 U.S.C. 154(b) by 0 days.

(21) Appl. No.: 10/186,384

(22) Filed: Jun. 28, 2002

Related U.S. Application Data
(60) Provisional application No. 60/301,918, filed on Jun. 29, 2001.

(51) Int. Cl.[7] .............................. H01B 7/00; H01B 7/18
(52) U.S. Cl. .............................. 174/102 R; 174/110 R; 174/113 R; 174/36
(58) Field of Search .............................. 174/36, 102 R, 174/102 C, 103, 105 R, 109, 110 R, 113 R

(56) References Cited

U.S. PATENT DOCUMENTS

| | | |
|---|---|---|
| 4,059,724 A | 11/1977 | Ide |
| 4,155,354 A | 5/1979 | Rasmussen |
| 4,173,221 A | 11/1979 | McLaughlin et al. |
| 4,345,111 A | 8/1982 | Petitcolas |
| 4,351,343 A | 9/1982 | Parrillo et al. |
| 4,383,225 A | 5/1983 | Mayer |
| 4,573,474 A | 3/1986 | Scibetta |
| 4,640,290 A | 2/1987 | Sherwin |
| 4,765,711 A | 8/1988 | Obst |
| 4,816,614 A | 3/1989 | Baigrie et al. |
| 4,850,367 A | 7/1989 | Rantala |
| 4,974,600 A | 12/1990 | Reyes |
| 5,287,074 A | 2/1994 | Meguro et al. |
| 5,293,001 A | 3/1994 | Gebs |
| 5,463,186 A | 10/1995 | Schricker |
| D366,528 S | 1/1996 | Crouse et al. |
| 5,491,299 A * | 2/1996 | Naylor et al. ................. 174/36 |
| 5,519,172 A | 5/1996 | Spencer et al. |
| 5,530,203 A | 6/1996 | Adams et al. |
| 5,546,950 A | 8/1996 | Schoeckert et al. |
| 5,569,158 A | 10/1996 | Suzuki et al. |
| 5,618,208 A * | 4/1997 | Crouse et al. ............. 439/609 |
| 5,817,974 A | 10/1998 | Bovenschen et al. |
| 5,876,326 A | 3/1999 | Takamura et al. |
| 5,895,298 A * | 4/1999 | Faupel et al. ............... 439/729 |
| 5,937,950 A | 8/1999 | Adams et al. |
| 5,976,070 A | 11/1999 | Ono et al. |
| 6,225,565 B1 | 5/2001 | Prysner |
| 6,577,236 B2 * | 6/2003 | Harman ...................... 340/552 |

OTHER PUBLICATIONS

Ott, H.W., *Noise Reduction Techniques in Electronic Systems*, 2d ed., John Wiley & Sons, New York, Mar. 1988, p. 62.

Stecker, M.M., and Terry Patterson, "Strategies for Minimizing 60 Hz Pickup During Evoked Potential Recording," *Electroencephalography and Clinical Neurophysiology* 100:370–371, 1996.

Wood, D.E., et al., "Comparative Analysis of Power–Line Interference Between Two– or Three–Electrode Biopotential Amplifiers," *Med. & Biol. Eng. & Comput.* 33:63–68, 1995.

* cited by examiner

*Primary Examiner*—William H. Mayo, III
(74) *Attorney, Agent, or Firm*—Christensen O'Connor Johnson Kindness PLLC

(57) ABSTRACT

A system and device for mitigating interference in patient physiological monitoring is provided, particularly in surgical environments. One or more sets of electrodes are placed on a patient's body and connected to corresponding terminals of an input extender. The terminals of the input extender are connected to a set of signal wires encased by a ferrous shielded cable. The ferrous shielded cable connects to a signal processing unit, which includes a differential amplifier and an active drive topology to drive the shield with a common mode signal. The signal processing unit connects to physiological monitoring equipment.

38 Claims, 6 Drawing Sheets

SYSTEM AND DEVICE FOR REDUCING SIGNAL INTERFERENCE IN PATIENT MONITORING SYSTEMS

CROSS-REFERENCE TO RELATED APPLICATION

This application claims the benefit of U.S. Provisional Patent Application no. 60/301,918, filed on Jun. 29, 2001, the disclosure of which is hereby expressly incorporated by reference, and priority from the filing date of which is hereby claimed under 35 U.S.C. § 119(e).

FIELD OF THE INVENTION

In general, the present invention relates to patient monitoring systems, and in particular, to a system and device for reducing electrical interference associated with patient monitoring systems.

BACKGROUND OF THE INVENTION

In a typical neurological monitoring environment, one or more sets of electrodes are attached to a patient's body. In turn, the electrodes are electrically connected to one or more pieces of monitoring equipment through signal wires. Depending on the placement of the electrodes, the monitoring equipment can be utilized to monitor various physiological signals to conduct patient tests, such as an electrocardiogram ("ECG"), an electroencephalogram ("EEG"), an electromyogram ("EMG"), and the like. Often, the physiological signals obtained from a patient may be of a low amplitude. For example, a typical physiological signal may have an amplitude as small as 0.2 $\mu V$. Accordingly, the low amplitude signals are highly susceptible to interference from environmental electrical/magnetic sources to the extent that the ability for the monitoring system to function properly is affected.

One skilled in the relevant art will appreciate that neurophysiological monitoring in surgical environments can present significant amounts of environmental interference. Generally described, a typical surgical environment can generate an electrically hostile environment due to the wide variety of electrical devices present in the surgical environment and their relative proximity to the patient and electrode wires. Additionally, hospital sterility regulations often require that some monitoring devices be outside of the direct surgical environment, thereby requiring a long set of electrode wires. Accordingly, the long length of the wires can increase the susceptibility of the low amplitude signals to interference generated by the various electrical devices along the path of the long length electrode wires. Additionally, long length wires can also be more susceptible to environmental electromagnetic interference. Accordingly, most remote monitoring systems attempt to mitigate interference caused by electrical and magnetic sources to better improve the accuracy of the system.

One attempt to mitigate the amount of interference relates to the shielding of some portion of the electrode wires with a braided copper shield. Although copper shielding may reduce some portion of electrical interference, a copper braided shield is generally ineffective against magnetic interference. More specifically, in a surgical environment, copper shielding is generally ineffective in reducing magnetic interference caused by cathode ray tube ("CRT") displays, drills, cutters, microscope lights, blood warmers, and anesthesia machines.

Another attempt to mitigate the amount of environmental interference relates to the use of a differential amplifier in the monitoring system. One skilled in the relevant art will appreciate that a differential amplifier will reject a common interfering signal received from a set of electrode inputs according to a factor known as a common mode rejection ratio ("CMRR"). For example, a high CMRR can result in smaller amplitude interference, which is especially effective for reducing low frequency electrostatic interference. However, because a CMRR is finite, the effectiveness of a differential amplifier may be reduced for lower amplitude signals, such as physiological signals, especially for environments, such as a surgical environment, that experience higher amounts of interference. Additionally, a differential amplifier's CMRR will generally be reduced with an increase in frequency. Thus, in surgical environments, the use of differential amplifiers alone is generally ineffective in mitigating the effects of electrical interference upon the physiological signals.

Another attempt to mitigate environmental interference relates to utilizing a differential amplifier in combination with physically twisting the signal wires together to cancel out the effects of low frequency magnetic interference. One skilled in the relevant art will appreciate that in a set of twisted wires (e.g., electrodes), the induced current in one twist tends to cancel out the same induced current generated in an adjacent twist. Generally described, the effectiveness of the twisting of two wires can be limited to reducing interference in environments in which an essentially uniform magnetic field strength is present. For example, in a surgical environment, magnetic interference may be caused by a near-field source that generates a non-uniform field from twist to twist. Additionally, if the spatial geometry of the twists is not uniform throughout the entire cable, the effectiveness is further reduced. Referring again to a surgical environment, the spatial geometry of the wires is often at issue because of the often great lengths of wire required. Thus, twisting signal wires is not sufficient to adequately mitigate interference associated with physiological monitoring.

Yet another attempt to mitigate environmental interference relates to the use of a ferrous metal hose to shield the wires. Although a shield including a ferrous hose can reduce low frequency magnetic interference, the application of a ferrous hose shielded cable can become impractical in several environments. Referring again to a surgical environment, ferrous metal hose shielded cables are generally not suited to be handled and easily manipulated, as they are bulky, semi-rigid, and weighty. Moreover, a ferrous hose shielded cable is not well suited for standard mass production cable manufacturing techniques by requiring the addition of insulation to the outside of the hose. Accordingly, this increases the overall cost of monitoring systems.

Thus, there is a need for a system and device capable of mitigating environmental interference in high interference environments.

SUMMARY OF THE PRESENT INVENTION

A system and device for mitigating interference in patient physiological monitoring is provided. One or more sets of electrodes are placed on a patient's body and connected to corresponding terminals of a terminal block of an input extender. The terminals of the terminal block are connected to a cable consisting of a set of signal wires encased by a ferrous braided shield. The shielded cable connects to a signal processing unit, which includes a differential amplifier and an active drive topology to drive the shield with a common mode signal. The signal processing unit connects to physiological monitoring equipment.

In accordance with an aspect of the present invention, a system for mitigating signal interference associated with a patient monitoring system is provided. The system includes a plurality of patient electrodes operable to obtain one or more patient physiological signals and a cable assembly operable for transmitting patient physiological signals received from the plurality of patient electrodes. The cable assembly includes electrically conductive signal wires corresponding to each of the plurality of patient electrodes. The cable assembly also includes a cavity formed by an outer ferrous shield. The system further includes a signal processing unit connected to the electrically conductive signal wires that includes an active drive topology operable to drive the outer ferrous shield with a common mode signal.

In accordance with a further aspect of the present invention, a means for mitigating signal interference associated with a patient monitoring system is provided. The means for mitigating signal interference further includes a means for obtaining a plurality of patient physiological signals, a shielding means for transmitting patient physiological signals and a processing means for actively removing signal interference.

In accordance with a further aspect of the present invention, a system for mitigating signal interference associated with a patient monitoring system is provided. The system includes an input extender that includes a terminal block having a plurality of terminals operable to electrically couple with a plurality of patient electrodes. The terminal block further includes a connector operable to electrically couple with a cable assembly having a plurality of conductive signal wires corresponding to the plurality of patient electrodes encased within a ferrous braided shield.

In yet still further aspects of the invention, the system for mitigating signal interference associated with a patient monitoring system includes a method for generating the common mode signal. The method includes obtaining patient physiological signals, generating a common mode signal, driving the outer ferrous shield of the input extender with the common mode signal, and processing the patient physiological signals.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The present invention is directed to a system and device for mitigating environmental electrical interference. More specifically, in an embodiment of the present invention, a system and device for mitigating environmental interference associated with neurophysiological monitoring in a surgical environment are provided. One skilled in the art will appreciate that the disclosed embodiments are illustrative in nature and should not be construed as limiting.

Figure 1:
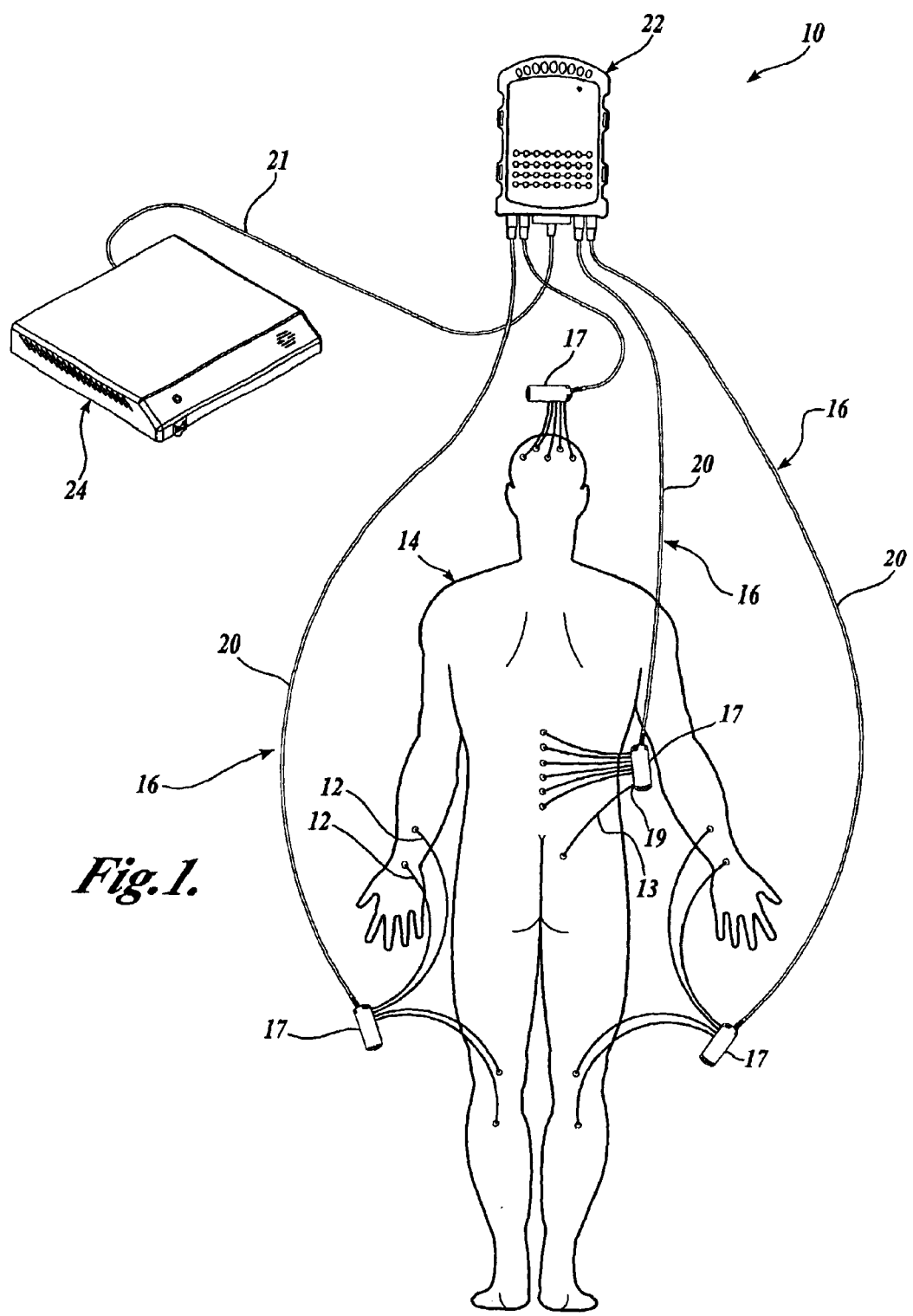
FIG. 1 is a diagram illustrative of a representative embodiment of a system and device for reducing signal interference in patient monitoring systems in accordance with the present invention.

FIG. 1 is a diagram illustrative of a representative embodiment of a neurophysiological patient monitoring system 10 formed in accordance with the present invention. As illustrated in FIG. 1, one or more pairs of electrodes 12 may be connected to a patient 14. The location and placement of the electrodes 12 will coincide with the particular type of monitoring desired, such as neurological monitoring. For example, the electrodes 12 may be connected to the patient 14 to monitor brain wave activity, electric muscle activity, electric heart activity, and the like. Each of the electrodes 12 is connected to an electrode input terminal 18 (see FIG. 2) of a terminal block 17 of one or more input extenders 16, which will be explained and described in greater detail below.

Each electrode input terminal of the terminal blocks 17 of the input extenders 16 corresponds to a conductive signal wire contained within a ferrous shielded cable 20 operatively connected to the terminal blocks 17. The length and dimension of the ferrous shielded cable 20 may vary according to the placement of the terminal block 17 relative to the patient 14 and the function of the electrodes 12 corresponding to the input extender 16.

One or more ferrous shielded cables 20 are then connected to one or more signal processing units 22 that may include a differential amplifier and various components for creating an active drive topology. The output from the signal processing unit 22 is then connected to one or more monitoring devices 24, such as display screens, computer terminals, and the like. In accordance with an actual embodiment of the present invention, the terminal blocks 17 are positioned in close proximity to the location of the patient electrodes 12 point of connection with the patient 14 so as to reduce the length of the patient electrodes 12. This arrangement, in combination with the ferrous shielded cable 20 and a signal processing unit 22 including a differential amplifier and an active drive topology, promotes the mitigation of environmental interference in monitoring devices, as will be discussed in further detail below.

Figure 2:
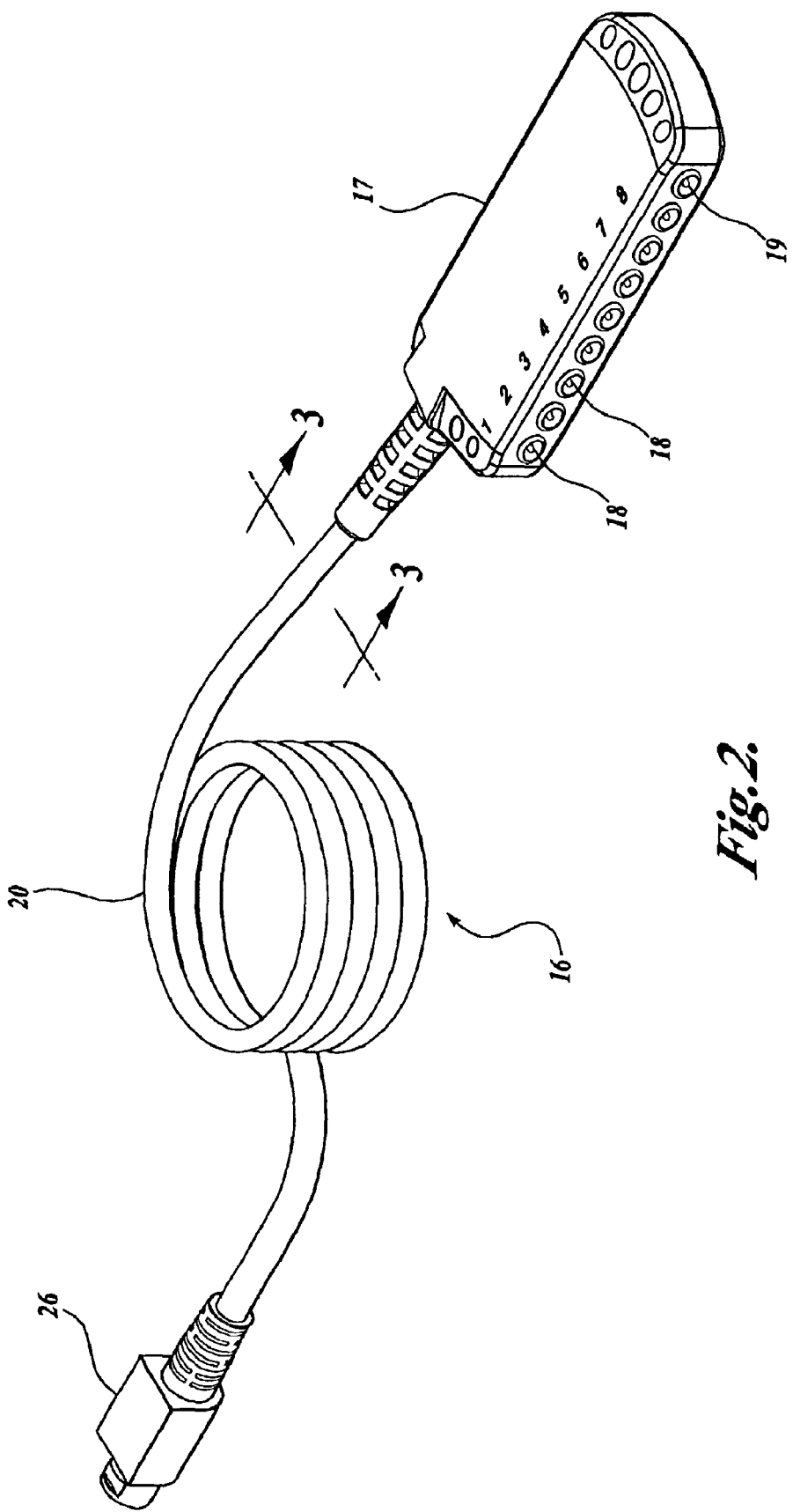
FIG. 2 is a perspective view of an input extender having a ferrous shielded cable, a connector operable to connect to a signal processing unit on a first end, and an input terminal block on a second end in accordance with the present invention.

FIG. 2 is a perspective view of an input extender 16 formed in accordance with the present invention. As illustrated in FIG. 2, the input extender 16 includes a ferrous shielded cable 20 which includes a connector 26 adaptable to releasably couple to a signal processing unit. One skilled in the relevant art will appreciate that the connector 26 may be constructed of any one of a variety of materials, such as molded plastics, and that the connector 26 may also include one or more attributes to facilitate connection/retention with the signal processing unit 22 (see FIG. 1), such as threads, twist locks, and the like.

Figure 3:
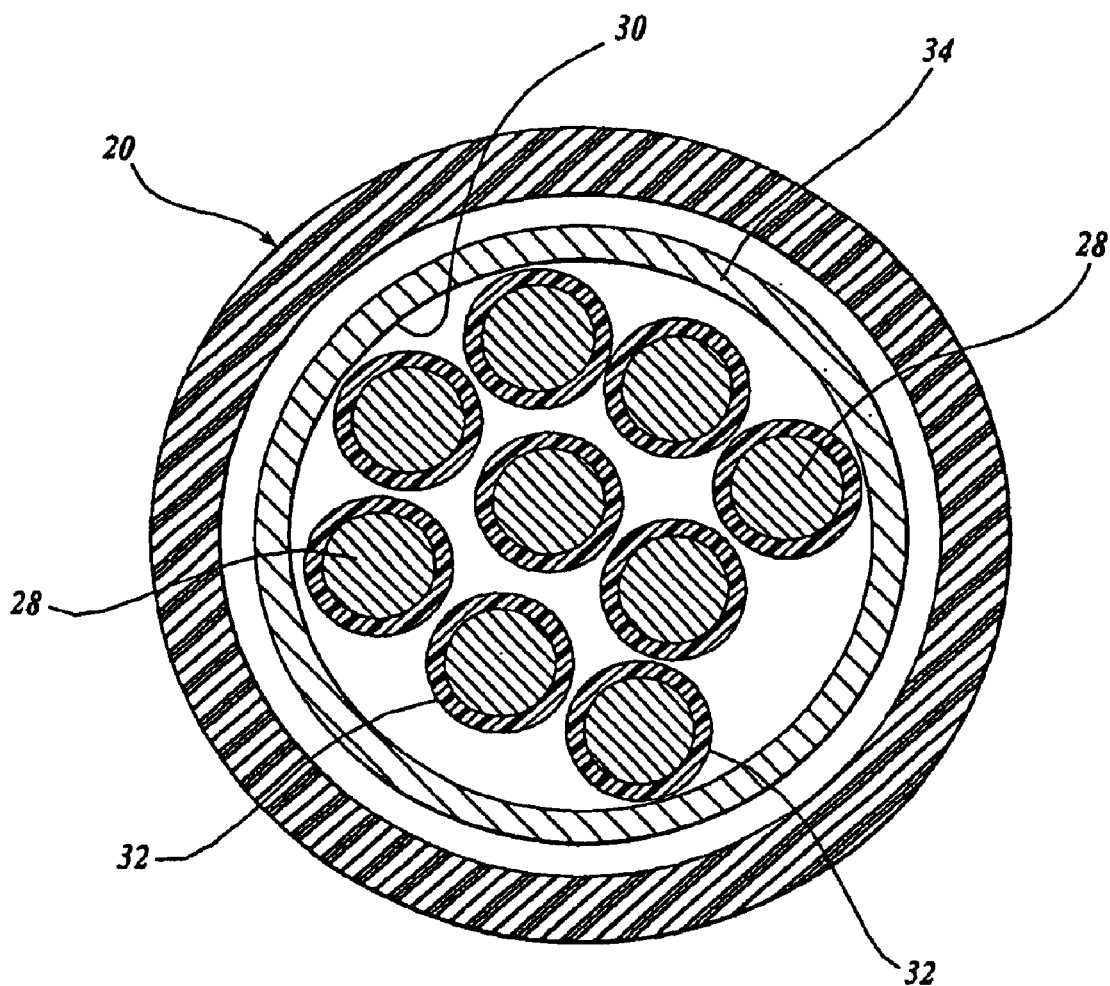
FIG. 3 is cross-sectional view of the ferrous shielded cable of FIG. 2 taken substantially through SECTION 3—3, showing a set of signal wires housed within a PVC-jacketed braided ferrous shield formed in accordance with the present invention.

Also connected to the ferrous shielded cable 20 is a terminal block 17. As illustrated in FIG. 2, in an illustrative embodiment of the present invention, the terminal block 17 is generally of a rectangular shape having a substantially flat top and bottom surface. The terminal block 17 also includes one or more side surfaces presenting an array of electrode inputs terminals 18. In an actual embodiment of the present invention, each electrode input terminal 18 in the array of inputs corresponds to a conductive signal wire 28, as best seen in FIG. 3, running through the ferrous shielded cable 20.

Still referring to FIG. 2, in an actual embodiment of the present invention, the bottom surface of the terminal block 17 allows the input extender 16 to rest in a stable manner on a substantially flat surface, such as an operating room table or patient bed. Additionally, the terminal block 17 may also include one or more gripping devices, such as a rubber coating, suction cups, textured surfaces, adhesives, Velcro, etc., to mitigate the amount of movement experienced by the input extender 16.

Although the terminal block 17 is illustrated as having a single array of electrode input terminals 18, one skilled in the relevant art will appreciate that the terminal block 17 may have multiple input electrode terminals 18 on various surfaces of the terminal block 17. For example, the terminal block 17 may have electrode inputs terminals 18 on a top surface, any side surface, an angled surface, and/or a bottom surface. Additionally, as will be illustrated below, the dimensions, including shape and number of inputs, of an input extender 16 may be modified to suit a particular type of neurological monitoring, or other type of monitoring.

The terminal block 17 of the input extender 16 further includes an isolated grounding electrode input terminal 19. Referring now to FIG. 1, an isolated grounding electrode 19 is affixed to the patient 14, electrically coupling the isolated grounding system of the patient monitoring system 10 directly to the patient 14 as is well know in the relevant art.

FIG. 3 is a cross-sectional view of the ferrous shielded cable 20 of. FIG. 2 taken substantially through Section 3—3 of FIG. 3. As illustrated in FIG. 3, the ferrous shielded cable 20 includes a number of conductive signal wires 28 housed in a central cavity 30 of the cable 20. In an actual embodiment of the present invention, each conductive signal wire 28 is a 28 gauge tinned copper wire whose inner conductive core is formed from 40 44-gauge strands. The conductive signal wire 28 is surrounded with an outer 0.010-inch thick PVC jacket 32. As explained above, in an illustrative embodiment of the present invention, the number of wires 28 in the ferrous shielded cable 20 corresponds to the number of electrode input terminals in the terminal block. However, in an alternative embodiment of the present invention, the number of conductive signal wires 28 in the ferrous shielded cable 20 may not match with the number of the electrode input terminals in the terminal block.

With continued reference to FIG. 3, the conductive signal wires 28 are surrounded by a ferrous metal braided shield 34. In an actual embodiment of the present invention, the ferrous metal braided shield 34 is formed from 40-gauge nickel/iron ferrous alloy strands. However, one skilled in the relevant art will appreciate that a variety of metals may be utilized to provide the ferrous metal braid 34. In turn, the ferrous metal braid 34 is surrounded by a protective coating, such as a PVC jacket. By utilizing a ferrous metal braid 34, the present invention mitigates low frequency environmental interference, while maintaining an effective flexibility and weight in the cable 20.

Figure 4:
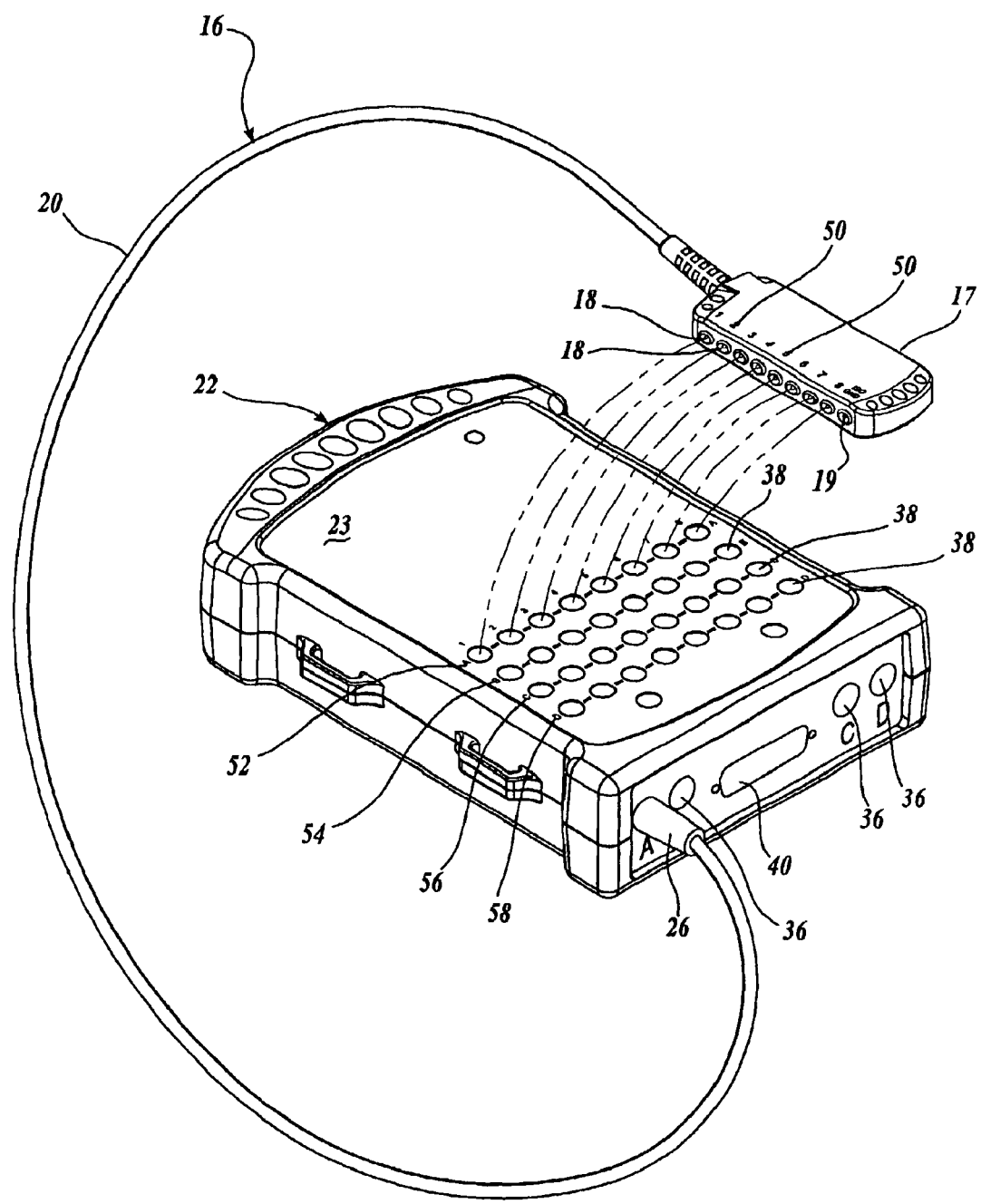
FIG. 4 is a perspective view of a ferrous shielded cable electrically coupling a terminal block of an input extender to a signal processing unit, illustrating the correlation between one or more input terminals of the terminal block and one or more connectors of the signal processing unit in accordance with the present invention.

FIG. 4 is a perspective view of a ferrous shielded cable 20, electrically coupling a terminal block 17 to a signal processing unit 22, illustrating the correlation between one or more input terminals 18 of the terminal block 17, with one or more connectors of the signal processing unit 22. In an actual embodiment of the present invention, the signal processing unit 22 includes a number of connectors 36 for accepting the connectors 26 of the cables 20 of a multiple number of input extenders 16. Additionally, the signal processing unit 22 also includes one or more rows of connectors 38, such as on a top surface 23, that correspond to the electrode input terminals 18 of one or more input extenders 16 as indicated by the phantom lines in FIG. 4. The signal processing unit 22 may also have one or more outputs 40 that transmit signals obtained from the input extender(s) 16 to physiological monitors.

The signal processing unit 22 and the terminal block 17 of the input extender 16 may be imprinted with indicia operable to identify one or more electrical connections. In the actual embodiment depicted, these indicia include both letters and numbers. The indicia are located adjacent to each electrode input terminal 18 on the terminal block 17 and adjacent to each input connector 38 and each ferrous shielded cable connection 36 on the signal processing unit 22. Similar indicia are placed adjacent to corresponding components that are in electrical continuity with one another.

For example, referring to the top of the signal processing unit 22 illustrated in FIG. 4, the input connectors 38 are arranged in a matrix having a first row 52 marked by the letter "A," a second row 54 marked by the letter "B," a third row 56 marked by the letter "C," and a fourth row 58 of connectors 38 marked by the letter "D." Corresponding letters are located adjacent to the cable connectors 36 to indicate to the user that a cable 20 coupled to a connector 36 marked with a letter "A," for example, is in electrically continuity with the row 52 of input connectors 38 marked with the letter "A." On the input extender 16, each electrode input terminal 18, except the isolated grounding electrode 19, is marked with a number from one to eight. The connectors 38 in each row 52, 54, 56, and 58 are also marked with a number from one to eight. The numerical indicia next to each electrode input terminal 18 indicate to which connector 38 in the row "A" 52 the electrode input terminal 18 is in correspondence. Marking the terminal blocks 17 and signal processing units 22 as described allows a user to quickly and visually identify which electrodes 12 (see FIG. 1) are in electrical continuity with which connectors 38. Monitoring devices can then be electrically coupled to specifically selected individual electrodes through coupling a wire (not shown) with the connectors 38 on the signal processing unit in an efficient and accurate manner.

In an actual embodiment of the present invention, the signal processing unit 22 includes a differential amplifier and an active drive topology that work in conjunction with one another. One skilled in the relevant art will appreciate that the combination of a shielded cable 20 with a differential amplifier may diminish the common mode rejection of the differential amplifier. More specifically, referring to FIG. 3, a capacitance formed between the conductive signal wires 28 and the ferrous metal shield 34 creates a voltage divider between the capacitance and the impedance of the patient at the point of connection of the electrode. Because the impedance of a patient is not uniform, some or all of the electrical signals on the conductive signal wires 28 would experience a different voltage division. Thus, any environmental interference signals common to all the electrical signals on the conductive signal wires 28 would be modified by the voltage division, thereby reducing the effectiveness of the differential amplifier.

Figure 5:
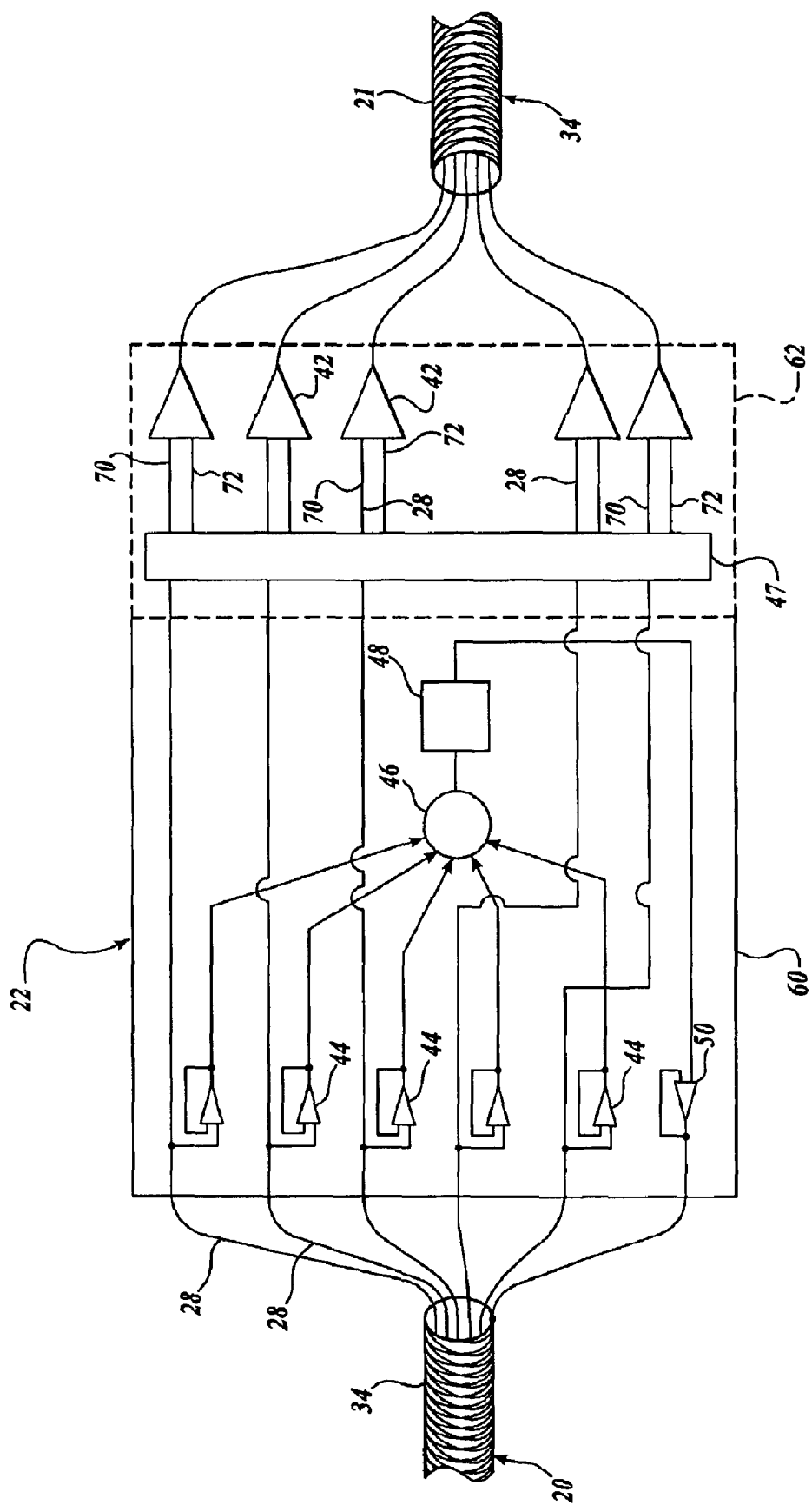
FIG. 5 is a schematic illustrative of an active drive topology utilized to drive a ferrous shielded cable in accordance with the present invention.

Referring now to FIG. 5, in an illustrative embodiment of the present invention, the signal processing unit 22 utilizes an active drive topology to drive a signal to the ferrous metal shield 34. As illustrated in the schematic of FIG. 5, a signal from each of the conductive signal wires 28 is fed to a buffer amplifier 44 to isolate the signals for transmission to an averaging component 46 located in a first section 60 of the signal processing unit 22. The use and operation of buffer amplifiers 44 are known to those skilled in the relevant art and will not be explained in greater detail. Examples of buffer amplifier 44 configurations are described in Adel S. Sedra and Kenneth C. Smith, *Microelectronic Circuits*, 3$^{rd}$ ed., 1991, the disclosure of which is incorporated by reference herein.

The averaging component 46 sums and normalizes the inputs to generate an average input signal. The output from the averaging component 46 is fed to a band pass filter 48 to filter out any additional DC and high frequency signals. The output of the filter 48 is then connected to another buffer amplifier 50, whose output is connected to the ferrous metal shield 34. Accordingly, by driving the ferrous metal shield with the averaged signal, the present invention reduces the capacitance between the ferrous shield 34 and the conductive wires 28. As stated before, this capacitance reduces the common mode rejection of the signal processing unit 22.

In an illustrative embodiment of the present invention, the signal wires 28 are also connected to a switching matrix 47 and a plurality of differential amplifiers 42 located in a second section 62 (depicted in dotted lines) of the signal processing unit 22. The use and operation of differential amplifiers 42 are known to those skilled in the relevant art and will not be explained in greater detail. Examples of differential amplifier 42 configurations are described in Adel S. Sedra and Kenneth C. Smith, *Microelectronic Circuits*, 3$^{rd}$ ed., 1991, the disclosure of which is incorporated by reference herein.

A switching matrix 47 is a well known component which allows the signals received from the signal wires 28 to be selectively directed to a pair of input terminals 70 and 72 associated with each differential amplifier 42 for processing. For example, the switching matrix 47 may selectively direct a signal carried along a first signal wire 28 to a first input terminal 70 and a signal carried along a second signal wire 28 to a second input terminal 72 of one of the differential amplifiers 42. Configured as such, the differential amplifier 42 would amplify the differential voltage present between the first and second signal wires 28, each signal wire in electrical communication with a separate patient electrode.

The switching matrix 47 is adaptable to selectively route any signal to any differential amplifier 42 input terminal in any manner desired by the user. For instance, the switching matrix 47 may reconfigure the routing of the signals so that the same differential amplifier 42 discussed above will receive the signal carried along the first signal wire 28 upon its first input terminal 70 and the signal carried along a third signal wire 28 upon its second input terminal 72. Thus, the differential amplifier 42 would now amplify the differential voltage present between the first and third signal wires 28. As should be apparent to one skilled in the art, the switching matrix is a highly adaptable device that may be configured in a wide range of configurations well beyond the illustrative examples described above.

The differential amplifiers 42 of the second section 62 of the signal processing unit 22 help to further mitigate signal interference. More specifically, the differential amplifiers 42 produce an output only in response to a potential difference sensed between the first input terminal 70 and the second input terminal 72 of the differential amplifier 42. By producing the output from only the difference present between the input terminals 70 and 72, signal interference from common-mode interference voltages are therefore suppressed as will be appreciated by one skilled in the art. In the illustrated embodiment, the first input terminal 70 and the second input terminal 72 receive the signals conveyed upon the conductive signal wires 28 as routed by the switching matrix 47.

Although the second section 62 of the signal processing unit 22 depicted in FIG. 5 is shown as housed within the signal processing unit 22, it will be appreciated by one skilled in the art that the differential amplifiers 42 and switching matrix 47 of the second section 62 may be placed in other locations in the neurophysiological patient monitoring system remote of the signal processing unit 22.

Still referring to FIG. 5, the signals transmitted along the conductive signal wires 28 housed within the ferrous shielded cable 20 may also be further processed within the signal processing unit 22. The signals may be processed by means (not shown) well know in the art, such as by filtering, converting, and amplifying. The signal processing unit processes the signals to mitigate interference effects, modify the format of the signals into a form receivable by the monitoring device if required, and to aid in the transmission of the signals within the cable 21, as is well known in the art.

Referring to FIG. 1, it is apparent to one skilled in the relevant art that the input extender 16 and the signal processing unit 22 may be modified in a variety of manners to suit the type of monitoring/testing being performed. For example, the number of electrodes 12, the number and location of the electrode input terminals 18, and/or the type of or quantity of connectors or terminals may vary to conform to the requirements of the test conducted or monitoring device utilized. However, the ferrous shielded cable 20, differential amplifier, and active drive topology may remain the same to mitigate environmental interference. For example, FIG. 6 shows a perspective view of a ferrous shielded cable 20 electrically coupling an alternate embodiment of an input extender 116 to an alternate embodiment of a signal processing unit 122.

Figure 6:
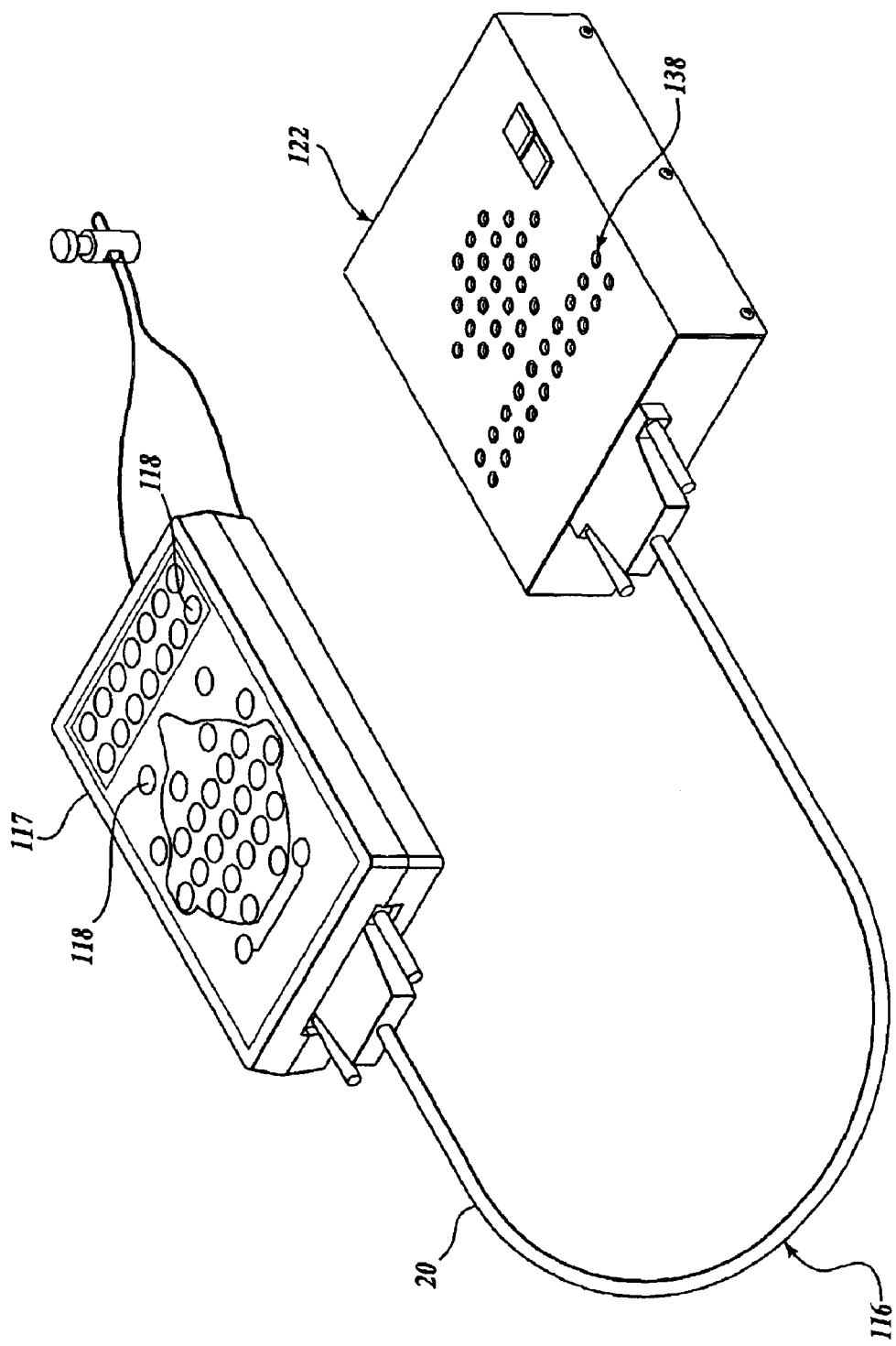
FIG. 6 is a perspective view of an alternate embodiment of an input extender consisting of a connection box and a ferrous shielded cable connected to a signal processing unit suitably arranged for use in electroencephalogram physiological testing in accordance with an alternate embodiment of the present invention.

In FIG. 6, the actual embodiment shown is suitably designed for accommodating electroencephalogram testing, having a sufficient number of electrode input terminals 118 on the top surface of the terminal block 117 for this purpose as is well known in the art. The signal processing unit 122 is also suitably designed for accommodating electroencephalogram testing, having a sufficient number of input connectors 138 on the top surface of the signal processing unit 122 to allow a monitoring device to selectively and individually receive a signal from each patient electrode coupled to the terminal block 117.

While illustrative embodiments of the invention have been illustrated and described, it will be appreciated that various changes can be made therein without departing from the spirit and scope of the invention.

What is claimed is:

1. A system for mitigating signal interference associated with a patient monitoring system, comprising:

a plurality of patient electrodes operable to obtain one or more patient physiological signals;

a cable assembly operable for transmitting patient physiological signals received from the plurality of patient electrodes, the cable assembly including electrically conductive signal wires corresponding to each of the plurality of patient electrodes, the cable assembly defining a cavity formed by an outer ferrous shield; and a signal processing unit connected to the electrically conductive signal wires, wherein the signal processing unit includes an averaging component for averaging the patient physiological signals obtained by the plurality of patient electrodes to derive an average patient physiological signal and an active drive topology operable to drive the outer ferrous shield with the average patient physiological signal.

2. The system as recited in claim 1, wherein the electrically conductive signal wires are physically twisted within the cable assembly to reduce interference.

3. The system as recited in claim 1, wherein the conductive signal wires are formed from tinned copper.

4. The system as recited in claim 1, wherein the signal processing unit further includes a differential amplifier operable to process patient physiological signals in a manner to reject a common interfering signal.

5. The system as recited in claim 1 further comprising at least one monitoring device electrically coupled to the signal processing unit, wherein the at least one monitoring device is operable to receive patient physiological signals processed by the signal processing unit.

6. The system as recited in claim 1, wherein the ferrous shield is comprised of a plurality of high permeability metal strand wires braided together.

7. The system as recited in claim 6, wherein the plurality of high permeability metal strand wires is formed from a nickel and iron ferrous alloy.

8. The system as recited in claim 1, wherein the signal processing unit has a plurality of connectors for electrically coupling a plurality of monitoring devices.

9. The system as recited in claim 1, wherein the signal processing unit has a plurality of connectors for electrically coupling a plurality of the cable assemblies.

10. The system as recited in claim 1, wherein the signal processing unit has a plurality of connectors in electrical continuity with a single patient electrode, wherein the connectors are operable to allow a monitoring device to be electrically coupled individually to each patient electrode.

11. The system as recited in claim 1, further comprising:

a terminal block, including a plurality of terminals operable to electrically couple with the plurality of patient electrodes; and a connector operable to electrically couple with the cable assembly.

12. The system as recited in claim 11, wherein the terminal block has at least one substantially horizontal bottom surface operable to allow the terminal block to rest in a stable manner upon a substantially horizontal surface when in use.

13. The system as recited in claim 12, wherein the terminals of the terminal block are oriented on a plane substantially parallel with the substantially flat surface of the terminal block.

14. The system as recited in claim 12, wherein the terminals of the terminal block are oriented on a plane substantially perpendicular with the substantially flat surface of the terminal block.

15. The system as recited in claim 12, wherein the cable assembly is attached to the terminal block in a manner so as to be oriented substantially parallel with the substantially flat surface of the terminal block.

16. The system as recited in claim 11, wherein the plurality of terminals of the terminal block are individually marked with a distinguishable indicia selected from a first set of indicia, wherein the signal processing unit has a set of connectors individually marked with a distinguishable indicia selected from a second set of indicia, wherein each terminal of the terminal block and each connector of the signal processing unit that are in electrical continuity are marked with indicia selected from the first and second sets of indicia to indicate an electrical connection.

17. The system as recited in claim 11, wherein the plurality of terminals is suitably arranged for electroencephalographic testing.

18. The system as recited in claim 1, wherein the signal processing unit further includes a buffer amplifier, wherein the buffer amplifier is operable to isolate patient physiological signals.

19. The system as recited in claim 1, wherein the active drive topology includes:

a differential amplifier operable to filter patient physiological signals; and a band pass filter operable to receive and filter the average patient physiological signal.

20. The system as recited in claim 19, wherein the active drive topology includes:

a first buffer amplifier operable to isolate patient physiological signals; and a second buffer amplifier operable to receive the filtered average patient physiological signal.

21. The system as recited in claim 1, wherein the cable assembly further includes a non-electrically conductive outer covering.

22. A system for mitigating signal interference associated with a patient monitoring system comprising:

means for obtaining a plurality of patient physiological signals;

transmitting means for transmitting patient physiological signals;

shielding means for shielding the patient physiological signals transmitted by the transmitting means;

averaging means for averaging the plurality of patient physiological signals to create an average patient physiological signal; and processing means for removing signal interference, the processing means including driving means for driving the shielding means with the average patient physiological signal derived from the averaging means.

23. The system as recited in claim 22, wherein the means for obtaining a plurality of patient physiological signals includes a terminal block having a plurality of terminals operable to electrically couple with a plurality of patient electrodes, wherein the terminal block is operable to electrically couple with a plurality of signal wires surrounded by the shielding means.

24. The system as recited in claim 23, wherein the terminal block has at least one substantially horizontal bottom surface operable to allow the terminal block to rest in a stable manner upon a substantially horizontal surface when in use.

25. The system as recited in claim 23, wherein the plurality of terminals of the terminal block are individually marked with a distinguishable indicia selected from a first set of indicia and wherein the processing means has a set of connectors individually marked with a distinguishable indicia selected from a second set of indicia, wherein the plurality of terminals of the terminal block and the connectors of the processing means that are in electrical continuity are marked with indicia selected from the first and second sets of indicia to indicate an electrical connection.

26. The system as recited in claim 22, wherein the processing means includes:
   a differential amplifier operable to amplify patient physiological signals;
   a band pass filter operable to receive and filter the average patient physiological signal.

27. The system as recited in claim 22, wherein the transmitting means includes electrically conductive signal wires physically twisted within the shielding means.

28. The system as recited in claim 22, wherein the processing means includes a signal processing unit having a differential amplifier operable to process patient physiological signals in a manner to reject a common interfering signal.

29. The system as recited in claim 22, further including at least one monitoring device electrically coupled to the processing means, wherein the at least one monitoring device is operable to receive patient physiological signals processed by the processing means.

30. The system as recited in claim 22, wherein the shielding means includes a plurality of high permeability metal strand wires braided together.

31. The system as recited in claim 30, wherein the plurality of high permeability metal strand wires are formed from a nickel and iron ferrous alloy.

32. The system as recited in claim 22, wherein the processing means includes a plurality of connectors for electrically coupling a plurality of cable assemblies.

33. The system as recited in claim 22, wherein the processing means has a plurality of connectors in electrically continuity with a patient electrode, wherein the connectors are operable to allow a monitoring device to be electrically coupled individually to each patient electrode.

34. In a patient monitoring system having:
   a plurality of patient electrodes operable to obtain one or more patient physiological signals;
   a cable assembly operable for transmitting patient physiological signals received from the plurality of patient electrodes, the cable assembly including electrically conductive signal wires corresponding to each of the plurality of patient electrodes, the cable assembly having a cavity formed by an outer ferrous shield; and
   a signal processing unit connected to the electrically conductive signal wires, wherein the signal processing unit includes an active drive topology operable to drive the outer ferrous shield with an average patient physiological signal;
   a method for reducing signal interference while obtaining patient physiological signals, the method comprising:
      obtaining patient physiological signals;
      generating an average patient physiological signal derived from averaging the patient physiological signals;
      driving the outer ferrous shield with the average patient physiological signal; and
      processing the patient physiological signals.

35. The method as recited in claim 34, wherein the method for generating the average patient physiological signal further comprises filtering the patient physiological signals, and summing and normalizing the patient physiological signals to generate the average patient physiological signal.

36. The method as recited in claim 34, further comprising shielding the physiological signals obtained from interference in a ferrous shield.

37. The method as recited in claim 36, wherein the ferrous shield comprises a plurality of high permeability metal strand wires braided together.

38. The method as recited in claim 37, wherein the plurality of high permeability metal strand wires are formed from a nickel and iron ferrous alloy.

* * * * *

UNITED STATES PATENT AND TRADEMARK OFFICE
CERTIFICATE OF CORRECTION

PATENT NO. : 6,870,109 B1
DATED : March 22, 2005
INVENTOR(S) : Richard A. Villarreal It is certified that error appears in the above-identified patent and that said Letters Patent is hereby corrected as shown below:

<u>Column 11,</u>
Line 12, "signals;" should read -- signals; and --

Signed and Sealed this

Twenty-eighth Day of June, 2005

JON W. DUDAS
*Director of the United States Patent and Trademark Office*